United States Patent [19]

Celmer et al.

[11] 4,450,237

[45] May 22, 1984

[54] *STREPTOMYCES ALBUS* SUBSPECIES INDICUS

[75] Inventors: Walter D. Celmer, New London; Walter P. Cullen, East Lyme, both of Conn.; Riichiro Shibakawa, Handa; Junsuke Tone, Chita, both of Japan

[73] Assignee: Pfizer Inc., New York, N.Y.

[21] Appl. No.: 529,802

[22] Filed: Sep. 6, 1983

Related U.S. Application Data

[62] Division of Ser. No. 374,223, May 3, 1982, Pat. No. 4,411,892.

[51] Int. Cl.$^3$ .................. C12N 1/20; C12P 19/62; C12R 1/47
[52] U.S. Cl. ..................................... 435/253; 435/76; 435/887
[58] Field of Search ..................... 435/253, 76, 887

[56] References Cited

U.S. PATENT DOCUMENTS 4,133,876  1/1979  Hamill et al. ................. 435/887
4,268,665  5/1981  Sakakibara et al. ........... 536/7.1
4,366,309  12/1982 Ganguly et al. ............... 536/7.1
4,385,116  5/1983  Baltz et al. ................... 435/76

FOREIGN PATENT DOCUMENTS 37  12/1978  European Pat. Off. .......... 435/887
2058765  4/1981  United Kingdom ............. 536/7.1

OTHER PUBLICATIONS

Encyclopedia of Chemical Technology, Kirk-Othmer, Third Edition, vol. 2, John Wiley & Sons, 1978, p. 951.

*Primary Examiner*—Alvin E. Tanenholtz
*Attorney, Agent, or Firm*—Charles J. Knuth; Albert E. Frost; J. Trevor Lumb

[57] ABSTRACT

An antibiotic complex, consisting of two major components, has been isolated from fermentations of a new subspecies of *Streptomyces albus* culture. The two major components from the complex are two new macrolide antibiotics, which are active as antibacterial agents against certain gram-positive and gram-negative microorganisms.

1 Claim, No Drawings

*STREPTOMYCES ALBUS* SUBSPECIES INDICUS

CROSS-REFERENCE TO RELATED APPLICATION

This application is a division of application Ser. No. 374,223, filed May 3, 1982 now U.S. Pat. No. 4,411,892.

BACKGROUND OF THE INVENTION

This invention relates to a new antibiotic complex, designated CP-55,358, and more particularly to the two major antibiotics contained therein, designated CP-56,063 and CP-56,064. The complex was derived from fermentation of a new Streptomyces culture, designated culture N409-40, obtained from a soil sample in India. Chemically, the two major antibiotics are macrolide compounds, having 16 members in the lactone ring. However, they both differ from known 16-membered macrolides, e.g. tylosin, in that they have a previously-unknown sugar unit attached to the C-5 position.

SUMMARY OF THE INVENTION

This invention provides new macrolide antibiotic compounds selected from the group consisting of

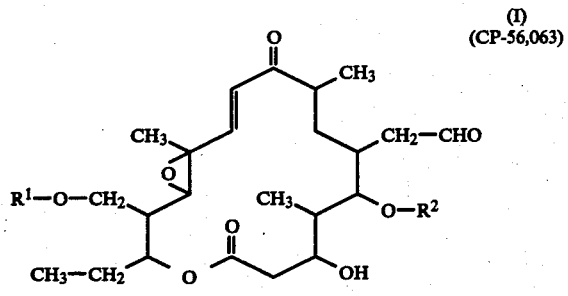
(I) (CP-56,063)

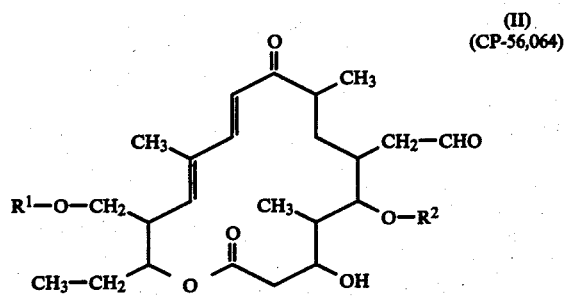
(II) (CP-56,064)

and the pharmaceutically-acceptable acid addition salts thereof, wherein $R^1$ is the group of the formula

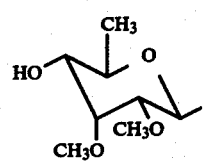

and $R^2$ is the group of the formula

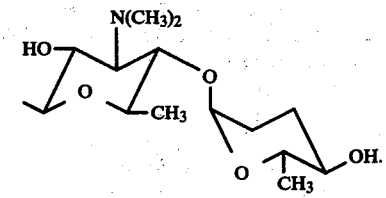

The compounds of formulae I and II are useful as antibacterial agents, and they are obtained by culture of a new subspecies of *Streptomyces albus* designated as culture N409-40. Said new subspecies is named as *Streptomyces albus* (Rossi Doria) Waksman and Henrici subsp. indicus Huang subsp. nov. (ATCC 39012).

DETAILED DESCRIPTION OF THE INVENTION

The antibiotic complex of this invention is produced by fermentation of a new microorganism designated as culture N409-40, which was obtained from a soil sample collected in India. Culture N409-40 was characterized and identified by Liang H. Huang, Ph.D., Pfizer Inc., Groton, Conn., U.S., as described hereinbelow.

On examination culture N409-40 was found to have narrow hyphae of the Actinomycetales, coiled chains of spores, and LL-diaminopimelic acid in the cell wall, characteristic of the genus Streptomyces.

Culture N409-40 was planted from a slant into liquid ATCC medium 172 and grown for four days at 28° C. on a shaker. It was then transferred to fresh ATCC medium 172 and incubated for another four days under the same conditions. The growth was centrifuged, washed three times with sterile distilled water, and planted on media commonly used for identification of members of the Actinomycetales. Incubation was made at 28° C. and a reading of results was made at varying times but most commonly at 14 days.

Identification media used for the characterization of the culture and references for their composition were as follows:

1. Tryptone Yeast Extract Broth—(ISP #1 medium, Difco).
2. Yeast Extract-Malt Extract Agar—(ISP #2 medium, Difco).
3. Oatmeal Agar—(ISP #3 medium, Difco).
4. Inorganic Salts-Starch Agar—(ISP #4 medium, Difco).
5. Glycerol-Asparagine Agar—(ISP #5 medium, Difco).
6. Peptone-Yeast Extract Iron Agar—(ISP #6 medium, Difco).
7. Czapek-Sucrose Agar—S. A. Waksman, The Actinomycetes, Vol. 2, medium no. 1, p. 328, 1961.
8. Glucose Asparagine Agar—Ibid, medium no. 2, p. 328.
9. Bennett's Agar—Ibid, medium no. 30, p. 331.
10. Emerson's Agar—Ibid, medium no. 28, p. 331.
11. Nutrient Agar—Ibid, medium no. 14, p. 330.
12. Gordon and Smith's Tyrosine Agar—R. E. Gordon and M. M. Smith, Jr. Bact. 69:147–150, 1955.
13. Casein Agar—Ibid.
14. Calcium Malate Agar—S. A. Waksman, Bact. Rev. 21:1–29, 1957.
15. Gelatin—R. E. Gordon and J. M. Mihm, Jr. Bact. 73:15–27, 1957.
16. Starch—Ibid.

17. Organic Nitrate Broth—Ibid.

18. Dextrose Nitrate Broth—S. A. Waksman, The Actinomycetes, Vol. 2, medium no. 1, p. 328, 1961, with 3 g. dextrose substituted for 30 g. sucrose and agar omitted.

19. Potato Carrot Agar—M. P. Lechevalier, Jr. Lab. and Clinical Med. 71:934–944, 1968 but use only 30 g. potatoes, 2.5 g. carrots and 20 g. agar.

20. 2% Tap Water Agar.

21. Skim Milk—Difco.

22. Cellulose utilization,
 (a) H. L. Jensen, Proc. Linn. Soc. N.S.W. 55:231–248, 1930.
 (b) M. Levine and H. W. Schoenlein, A Compilation of Culture Media, medium no. 2511, 1930.

23. Carbohydrates—ISP #9 medium, Difco.

24. Temperature Range—ATCC medium 172 in ATCC Culture Collection Catalogue, 12th ed., p. 329, 1976.

Culture N409-40 exhibited the following characteristics, with colors being given in common terminology and also with reference to color chips from the *Color Harmony Manual*, 4th Edition:

Yeast Extract-Malt Extract Agar—Growth moderate to good, colorless to cream (2ca), thin to raised, wrinkled, no aerial mycelium; reverse same as surface; soluble pigment pale yellowish (21c).

Oatmeal Agar—Growth moderate, off-white, slightly raised, smooth, aerial mycelium white, sparse; reverse same as surface; no soluble pigment.

Inorganic Salts-Starch Agar—Growth moderate to good, off-white to pale yellowish (2ea to 2ga), thin to raised, smooth to wrinkled, aerial mycelium white, sparse; reverse same as surface; soluble pigment brownish (31e).

Glycerol-Asparagine Agar—Growth moderate, pale lavender (3ec), thin, smooth, no aerial mycelium; reverse same as surface; soluble pigment very pale lavender (3ca).

Gordon and Smith's Tyrosine Agar—Growth moderate, cream (2ca), thin, smooth, no aerial mycelium; reverse same as surface, soluble pigment pale yellowish (2ea).

Czapek-Sucrose Agar—Growth moderate, pale yellowish (2ca), thin, smooth, aerial mycelium white, sparse; reverse same as surface; soluble pigment pale yellowish (2ca).

Glucose Asparagine Agar—Growth poor to moderate, cream (2ca), thin to raised, smooth to wrinkled, no aerial mycelium, reverse same as surface; no soluble pigment.

Calcium Malate Agar—Growth moderate, pale yellowish to yellowish (1½ ca, 1κ ea to 1½ ia), thin, smooth, no aerial mycelium, reverse pale yellowish; no soluble pigment.

Casein Agar—Growth moderate, pale yellowish (1½ ca), thin, smooth, no aerial mycelium; reverse same as surface; soluble pigment pale yellowish (2ga).

Bennett's Agar—Growth good, cream to yellowish (2ca, 2ea to 2ga), raised, coarsely wrinkled to cracked, no aerial mycelium; reverse same as surface; soluble pigment pale yellowish (2ea).

Emerson's Agar—Growth good, cream (2ca), raised, finely wrinkled, no aerial mycelium; reverse same as surface; soluble pigment pale yellowish brown (2lc).

Nutrient Agar—Growth poor, colorless to cream (2ca), thin, smooth, no aerial mycelium; reverse same as surface; no soluble pigment.

Gelatin Agar—Growth moderate to good, cream (2ca), slightly raised, smooth or wrinkled near the edge, no aerial mycelium; reverse same as surface, no soluble pigment.

Starch Agar—Growth good, cream (2ca), raised, wrinkled, no aerial mycelium; reverse same as surface; no soluble pigment.

Potato Carrot Agar—Growth poor to moderate, pale yellowish (1½ ca), thin, smooth, aerial mycelium white, scant; reverse same as surface; no soluble pigment.

Tap Water Agar—Growth poor, colorless to white, thin, smooth, aerial mycelium white, sparse; reverse same as surface; no soluble pigment.

Culture N409-40 exhibited the following biochemical properties: melanin not produced; hydrogen sulfide produced; gelatin liquefied; starch hydrolyzed; nitrate reduced to nitrite; no growth and no decomposition on both cellulose broths; no coagulation and no peptonization on milk; casein digestion positive; calcium malate digestion positive; tyrosine digestion positive; glucose, inositol, fructose, and sucrose utilized as a carbohydrate source; arabinose, mannitol, melibiose, raffinose, rhamnose, and xylose not utilized as a carbohydrate source.

When morphological observations were made on Czapek-sucrose agar after 16 days of incubation, culture N409-40 exhibited the following properties: spore mass in white color series; sporophores monopodially branched, borne closely to one another; spore chains in compact spirals or rarely in loose spirals which have 3–7 turns per spore chain, with the spiral in small diameter, often aggregated in clusters, 10 to 50 spores per spore chain; spores globose, oval to elliptical, 0.7–1.0 $\mu$m in diameter, or 0.8–1.1×0.7–0.9 $\mu$m, smooth, as revealed by scanning electron microscopy.

The relationship of temperature to growth rate for culture N409-40 was as follows: 21° C., good growth; 28° C., excellent growth; 37° C., poor growth; 45° C., poor growth.

Whole-cell and sugar analyses were carried out on new culture N409-40 using the methods in Becker, B. et al., Appl. Microbiol., 12:421–423, 1964; and in Lechevalier, M. P., J. Lab. Clin. Med., 71:934–944, 1968. The results were as follows: the whole-cell hydrolyzates contain LL-diaminopimelic acid, galactose and ribose.

Culture N409-40 is characterized by spores in white color-series, coiled spore chains, smooth spores, and negative melanin reaction. It closely resembles *Streptomyces albus* and thus the type culture of *S. albus* ATCC 3004 is used for comparison. Both cultures produce coiled spore chains and white spores in mass with a smooth surface and show negative melanin reaction and positive hydrogen sulfide production.

Unlike N409-40, *S. albus* ATCC 3004 utilizes arabinose, mannitol, and xylose; but it does not utilize inositol. On yeast extract-malt extract agar, Czapek sucrose agar, glucose asparagine agar, Emerson's agar, and nutrient agar, colonies of *S. albus* ATCC 3004 are white, whereas those of N409-40 are cream because of the lack of aerial mycelium. On oatmeal agar, glycerol-asparagine agar, glucose asparagine agar, and nutrient agar, *S. albus* ATCC 3004 grows as isolated colonies rather than as a confluent smear as does N409-40. In addition, *S. albus* ATCC 3004 does not produce a soluble pigment on yeast extract-malt extract agar, inorganic salts-starch agar, Czapek sucrose agar and Emerson's agar. On the basis of the above similarities and differences, culture N409-40 is considered to represent a new subspecies of *S. albus* and is named *Streptomyces*

*albus* (Rossi Doria) Waksman and Henrici subsp. indicus Huang subsp. nov., and is on deposit at the American Type Culture Collection, Rockville, Md. U.S., under the accession number ATCC 39012. The permanency of the deposit of this culture at the American Type Culture Collection at Rockville, Md. and ready accessibility thereto by the public are afforded throughout the effective life of the patent in the event the patent is granted. Access to the culture is available during pendency of the application under 37 CFR 1.14 and 35 USC 112. All restrictions on the availability to the public of the culture deposited will be irrevocably removed upon granting of the patent.

The antibiotic complex of this invention is obtained by fermenting *S. albus* subsp. indicus ATCC 39012, and extracting the complex from the fermentation broth. The compounds of formula I and II can be obtained from the complex by classical methods such as chromatography or counter-current distribution.

Fermentation of the *S. albus* subsp. indicus ATCC 39012 can be conducted under conditions similar to those used for obtaining the macrolide antibiotic, tylosin, from *Streptomyces fradiae*. In general, the *S. albus* can be grown from 24°–36° C. in an aqueous, nutrient medium, with agitation and aeration, under submerged conditions. The nutrient medium contains an assimilable carbon source, such as sugars, starches or glycerol; organic nitrogen substances, such as soybean meal, casamino acids and yeast extract; growth substances, such as grain solubles, fish meal and cotton seed meal; mineral salts containing trace elements, such as iron, cobalt, copper and zinc; and calcium carbonate or phosphates as buffering agents.

Inoculum is prepared by scraping vegetative cells from slants or Roux bottles incubated with the N409-40 culture. A solid medium suitable for initial growth on slants and Roux bottles is ATCC medium No. 172.

| ATCC 172 | |
|---|---|
| Ingredient | Amount (gms./liter) |
| Glucose | 10 |
| Soluble Starch | 20 |
| Yeast Extract | 5 |
| NZ Amine A (Humko)* | 5 |
| Calcium Carbonate | 1 |
| Distilled Water to 1000 ml.; pH to 7.0 with KOH | |
| Add Agar | 20 |

*A purified enzymatic digest of casein.

Vegetative cells from slants are used to inoculate either shake flasks or inoculum tanks; or alternately the inoculum tanks are inoculated from shake flasks. In shake flasks, growth will generally have reached its maximum in one or three days, whereas in the inoculum tanks growth will usually be at the most favorable period in 20 to 40 hours after inoculation. A fermentor is inoculated with vegetative broth from the inoculum flask or tank, under completely aseptic conditions, and fermented for a period of 12 to 30 hours. Aeration is maintained in the shake flask by agitation on a shaker or in tanks by forcing sterile air through a sparger at the rate of ½ to 2 volumes of air per volume of broth per minute. The speed of agitation (stirring) depends upon the type of agitator employed; a shake flask is usually run at 150 to 200 cycles per minute and a fermentor at 300 to 600 revolutions per minute. Sterility is maintained at all times. The temperature is regulated between 24° C. and 36° C. Foaming during the fermentation can be controlled with sterile antifoam such as refined soybean oil, or other suitable antifoam agents in the makeup and as needed aseptically after inoculation.

The progress of antibiotic production during fermentation, and the bioactivity of the fermentation broth and recovery streams, can be monitored by biological assay of the broth employing a sensitive strain of *Staphylococcus aureus* or *Bacillus subtilis*. *S. aureus* ATCC 6538 and *B. subtilis* ATCC 6633 are suitable strains for this purpose. Standard plate assay technique is employed, in which the zone of inhibition surrounding a filter paper disc saturated with the broth is used as a measure of antibiotic potency. Also, thin-layer chromatography employing silica gel is a useful tool for analyzing the antibiotic produced in fermentation media and the composition of crude and purified materials extracted from the fermentation broths. The components in the broth and recovery streams can be detected by using Analtech silica gel GF plates in chloroform/methanol (9:1) and visualizing the antibiotics under ultraviolet light at 254 millimicrons. The plate can also be overlayed with agar seeded with either *S. aureus* or *B. subtilis* and incubated at 37° C. for 16 hours to detect the antibiotics.

The antibiotic complex of this invention can be recovered from a fermentation broth of *S. albus* subsp. indicus ATCC 39012 by extraction of the whole broth using a volatile, water-immiscible organic solvent such as ethyl acetate, n-butanol, chloroform or methyl isobutyl ketone, at a pH in the range from 7 to 10. Alternatively, the mycelium can be removed from whole broth, and then the filtrate is extracted in the same manner as for whole broth. This affords a solution of the antibiotic complex in an organic solvent. The antibiotic complex can be back extracted into water at an acidic pH (e.g. using water adjusted to pH 3.5 with phosphoric acid) and then re-extracted into a water-immiscible volatile, organic solvent such as ethyl acetate, n-butanol, chloroform or methyl isobutyl ketone, at a pH of 7 to 10. The organic solvent is removed by evaporation in vacuo and the residue is stirred with hexane. The hexane is removed, leaving the antibiotic complex, usually as a solid. The crude antibiotic complex can be separated into components by chromatography or counter-current distribution.

The compounds of the formula I and II will form acid addition salts, and these acid addition salts are considered to be within the scope and purview of this invention. Said acid addition salts are prepared by standard methods for macrolide compounds, for example by combining a solution of the compound of formula I or II in a suitable solvent (e.g. ethyl acetate, acetone, methanol, ethanol or butanol) with a solution containing a stoichiometric equivalent of the appropriate acid. If the salt precipitates, it is recovered by filtration; alternatively, it can be recovered by evaporation of the solvent. Of particular value are the sulfate, hydrochloride, hydrobromide, nitrate, phosphate, citrate, tartrate, pamoate, perchlorate, sulfosalicylate, benzenesulfonate, 4-toluenesulfonate and 2-naphthylenesulfonate salts.

The antibiotic complex of this invention shows antibacterial activity against certain gram-positive and gram-negative microorganisms. This antibacterial activity can be demonstrated by measuring the minimum inhibitory concentration (MIC) of the complex against a variety of organisms, according to standard procedures. Thus, the MIC's can be measured by the procedure recommended by the International Collaborative Study on Antibiotic Sensitivity Testing (Ericcson and Sherris, *Acta. Pathologica et Microbiologia* Scandinav, Supp. 217, Section B: 64–68 [1971]), which employs brain heart infusion (BHI) agar and the inocula replicating device. Overnight growth tubes are diluted 100 fold for use as the standard inoculum (20,000–10,000 cells in approximately 0.002 ml. are placed on the agar surface; 20 ml. of BHI agar/dish). Twelve 2 fold dilutions of the test compound are employed, with initial concentration of the test drug being 50 mcg./ml. Single colonies are disregarded when reading plates after 18 hours at 37° C. The susceptibility (MIC) of the test organism is accepted as the lowest concentration of compound capable of producing complete inhibition of growth as judged by the naked eye.

The antibacterial activity of the antibiotic complex, and the two major components of formulae I and II, and the pharmaceutically-acceptable salts thereof, makes them suitable for the treatment of bacterial infections caused by susceptible organisms in mammalian subjects. In particular, an antibiotic substance of this invention or a salt thereof is useful in treating bacterial infections in large farm animals, e.g. horses, cows and swine, and also domestic pets, e.g. cats and dogs.

When using an antibacterial compound of this invention, or a salt thereof, in a mammal, the compound can be administered alone, or it can be mixed with other antibiotic substances and/or pharmaceutically-acceptable carriers or diluents. Said carrier or diluent is chosen on the basis of the intended mode of administration. For example, when considering an oral mode of administration, an antibacterial compound of this invention can be used in the form of syrups, elixirs, aqueous solutions and suspensions, and the like, in accordance with standard pharmaceutical practice. The proportional ratio of active ingredient to carrier will naturally depend on the dosage contemplated; however, said proportional ratio will normally be in the range from 1:6 to 6:1 by weight, and preferably 1:1 to 1:4. An antibacterial compound of this invention can also be administered parenterally, which includes intramuscular, intraperitoneal, subcutaneous and intravenous administration. For these purposes, sterile solutions of the active ingredient are usually prepared, and the pH of the solutions are suitably adjusted and buffered. For intravenous use, the total concentration of solutes should be controlled to render the preparation isotonic.

As indicated earlier, the antibacterial compounds of this invention are of use in pets and farm animals and the daily dosages to be used will not differ significantly from other macrolide antibiotics, such as tylosin. The prescribing veterinarian will ultimately determine the appropriate dose for a given subject, and this can be expected to vary according to the weight and response of the individual animal as well as the nature and the severity of the animal's symptoms. The compounds of this invention will normally be used orally at dosages in the range from 20 to about 50 mg. per kilogram of body weight per day, and parenterally at dosages from about 10 to about 30 mg. per kilogram of body weight per day, usually in divided doses. In some instances it may be necessary to use doses outside these ranges.

The following examples are provided solely for further illustration.

EXAMPLE I

Fermentation of *Streptomyces albus* ATCC 39012

Shake flasks were prepared using the following medium:

| Ingredient | Amount (Grams/Liters) |
| --- | --- |
| Cerelose | 10 |
| Corn Starch | 20 |
| Yeast Extract (Difco) | 5 |
| NZ Amine A (Humko)* | 5 |
| Cobalt Chloride | 0.002 |
| Tap water to one liter, pH to 7.1–7.2 | |

*A purified enzymatic digest of casein.

The medium was distributed in 40 ml. portions to 300 ml. shake flasks, and it was then sterilized at 120° C. and 15 p.s.i. for 30 minutes. After cooling, the medium was inoculated with a vegetative cell suspension from the *Streptomyces albus* subsp. indicus slant culture ATCC 39012, grown on ATCC 172 medium in agar. The flasks were shaken at 28° C. on a rotary shaker having a displacement of 1½ to 2½" at 150 to 200 cycles per minute (CPM) for two to four days, then used to inoculate four liter fermentation vessels containing two liters of one of the following media:

| Ingredient | Amount (grams/liter) | Ingredient | Amount (grams/liter) |
| --- | --- | --- | --- |
| Cerelose | 10.0 | Cerelose | 1.0 |
| Corn Starch | 20.0 | NZ Amine Ytt* | 2.5 |
| Yeast BYF 300 | 5.0 | Corn Starch | 5.0 |
| NZ Amine Ytt (Humko)* | 5.0 | Corn Steep Liquor | 5 cc |
| Cobalt Chloride | 0.002 | Cobalt Chloride | 0.002 |
| Calcium Carbonate | 1.0 | Calcium Carbonate | 3.0 |
| pH 6.9–7.0 to 1 liter with water | | | |

*An enzymatic digest of casein.

One milliliter of antifoaming agent was added, and the vessels were sealed and sterilized at 120° C. and 15 p.s.i. for 45 minutes. The vessels were inoculated with one (2%) or two (4%) shake flasks, fermented for 12 to 30 hours at 30° C., stirred at 1700 revolutions per minute (RPM) and air sparged through the broth at one volume per volume per minute. When fermentation was complete (based on antibiotic disc assay versus *B. subtilis* ATCC 6633), the fermentation was stopped, and the whole broth was filtered. The filtrate was extracted with methyl isobutyl ketone or ethyl acetate at pH 9.0. The organic phase was removed from the aqueous phase by aspiration, and then the organic phase was sparkled and concentrated in vacuo to a viscous oil.

EXAMPLE II

Isolation and Characterization of the Two Major Components from the *Streptomyces albus* subsp. indicus ATCC 39012 Fermentation Two 1,000 gallon fermentations of *Streptomyces albus* subsp. indicus ATCC 39012 were extracted with 300 gallons of methyl isobutyl ketone. The methyl isobutyl ketone was extracted twice with acidic water (pH 3.5) using 15 gallons of water each time. These extracts were combined and the pH was raised to 9.0 with 6 N NaOH. The aqueous phase was then extracted with 7 gallons of chloroform. The chloroform was evaporated to a yellow oil (25 g.). This oil was triturated with one liter of heptane and the solids thus generated were collected by filtration and washed with fresh heptane to give 2.6 g. of a solid.

The above 2.6 g. of solid was chromatographed on a 2.5×100 cm. column packed with column grade silica gel 60 (Merck) in CHCl₃—MeOH—NH₄OH (92:8:1). The same solvent system was used to elute the column. The flow rate was 10 ml./minute and one cut was taken every minute. The cuts were examined by thin layer chromatography and the cuts containing the two major antibiotic components were combined and evaporated in vacuo. This afforded 1.0 g. of the antibiotic complex as a solid. This latter solid was rechromatographed on silica gel using the same conditions, to give 150 mg. of antibiotic complex. The infrared spectrum of the antibiotic complex (KBr disc) showed significant absorption bands at 2.95, 3.45, 5.80, 6.20, 6.90, 7.25, 7.65, 8.30, 9.30, 9.95, 10.25 and 11.85 microns. The ultraviolet spectrum of the antibiotic complex (in methanol) showed absorption maxima at 238 millimicrons ($E_{1\%}$ 141) and 279 millimicrons ($E_{1\%}$ 80.5).

Analysis: Found: C, 59.00; H, 8.45; N, 1.48%.

EXAMPLE III

Separation of the Antibiotic Complex

The antibiotic complex was separated into its components utilizing a reverse phase $C_{18}$ silica gel column. The eluant used was methanol-water-2-aminoethanol (55:45:0.5). The flow rate was 5 ml./minute and one cut was taken every minute. The column was monitored with a 254 nm ultraviolet detector. The major component eluted was that represented by formula I while the minor component is shown by formula II. The following physicochemical data were determined for the individual components.

Formula I

Molecular formula $C_{44}H_{75}O_{17}N$.
Molecular weight 889.
Melting point 210°–215° C. (dec.)
Analysis: C, 58.90; H, 7.97; N, 1.69%.
Optical rotation [alpha]$_D$= −57° (c=1, CH₃OH).
Ultraviolet 238 nm; $E_{1\%}^{1\ cm}$=151.
White amorphous solid.

The significant bands in the infrared spectrum over the region 4,000 to 200 cm⁻¹ are: (KBr disk) 3440, 2985, 2935, 1720, 1690, 1620, 1170 and 1080 cm⁻¹.

Formula II

Molecular formula $C_{44}H_{75}O_{16}N$.
Molecular weight 873.
Melting point 118°–130° C. (dec.).
Ultraviolet 282 nm; $E_{1\%}^{1\ cm}$=186.
Amorphous solid.

The solubilities of the two compounds are similar: soluble in chloroform, methanol, ethanol and ethyl acetate; insoluble in heptane and water.

We claim:

1. A biologically pure culture of the microorganism *Streptomyces albus* subsp. *indicus*, ATCC 39012, said culture being capable of producing, in a recoverable quantity, upon cultivation in an aqueous nutrient medium containing assimilable sources of nitrogen and carbon, a compound selected from the group consisting of

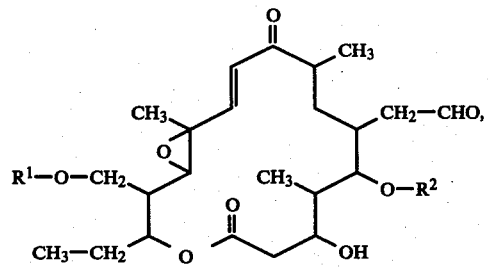

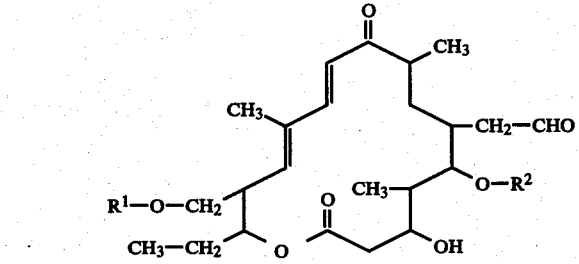

and the pharmaceutically-acceptable acid addition salts thereof; wherein $R^1$ is the group of the formula

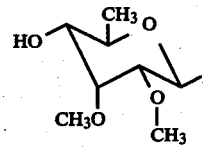

and $R^2$ is the group of the formula

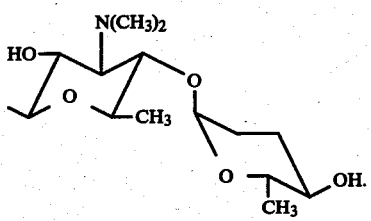

* * * * *